United States Patent [19]
Leschek et al.

[11] 3,935,484
[45] Jan. 27, 1976

[54] REPLACEABLE ACOUSTIC TRANSDUCER ASSEMBLY

[75] Inventors: Walter C. Leschek, Pittsburgh, Pa.; Philip E. Carpentier, Elmira, N.Y.

[73] Assignee: Westinghouse Electric Corporation, Pittsburgh, Pa.

[22] Filed: Feb. 25, 1974

[21] Appl. No.: 445,523

[52] U.S. Cl. ............... 310/8.2; 310/8.9; 310/9.1; 340/8 FT
[51] Int. Cl.² ............................................ H01V 7/00
[58] Field of Search .............. 310/9.1, 9.2, 9.3, 9.4, 310/8.9, 8.7, 8.2, 8.3; 340/8 MM, 8 FT, 8 S

[56] References Cited
UNITED STATES PATENTS

| | | | |
|---|---|---|---|
| 2,467,353 | 4/1949 | Wolfskill | 310/9.7 X |
| 2,803,129 | 8/1957 | Bradfield | 310/8.2 |
| 3,146,360 | 8/1964 | Marshall | 310/8.9 X |
| 3,200,369 | 8/1965 | Neubauer et al. | 310/9.1 |
| 3,390,287 | 6/1968 | Sonderegger | 310/8.7 X |

FOREIGN PATENTS OR APPLICATIONS 1,086,640  11/1967  United Kingdom ............... 310/8.2

Primary Examiner—Mark O. Budd
Attorney, Agent, or Firm—W. G. Sutcliff

[57] ABSTRACT

An easily replaceable acoustic transducer assembly is provided for usage in high temperature applications. The improved structure permits efficient acoustical coupling between the component parts of the tranducer assembly, and is more readily reproducible in sensitivity and frequency response. A generally tubular high temperature resistant metal enclosure is provided with an acoustical window which is coupled to the piezoelectric transducer element. The piezoelectric element is acoustically coupled to a damping block member. Acoustical coupling between the active elements of the transducer assembly is had from a compressive means integral within the enclosure member.

14 Claims, 3 Drawing Figures

U.S. Patent  Jan. 27, 1976  3,935,484
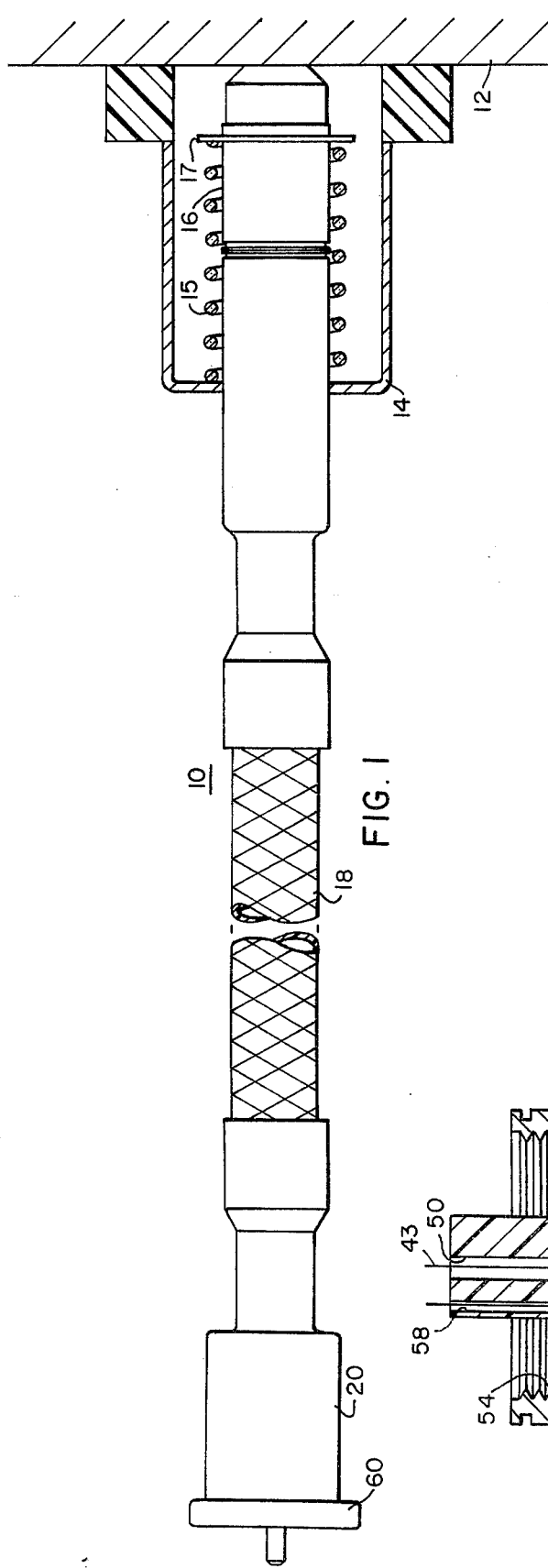
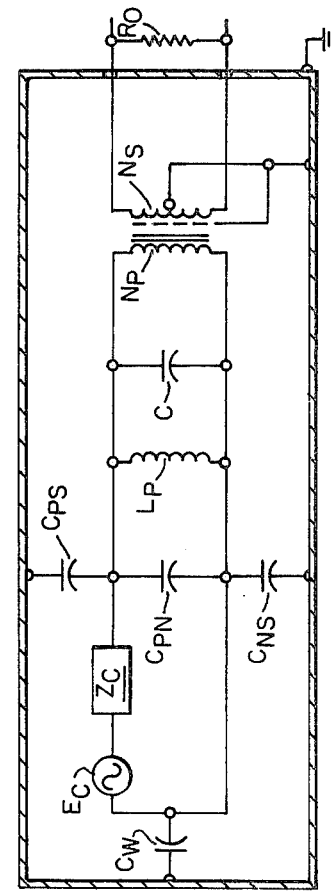
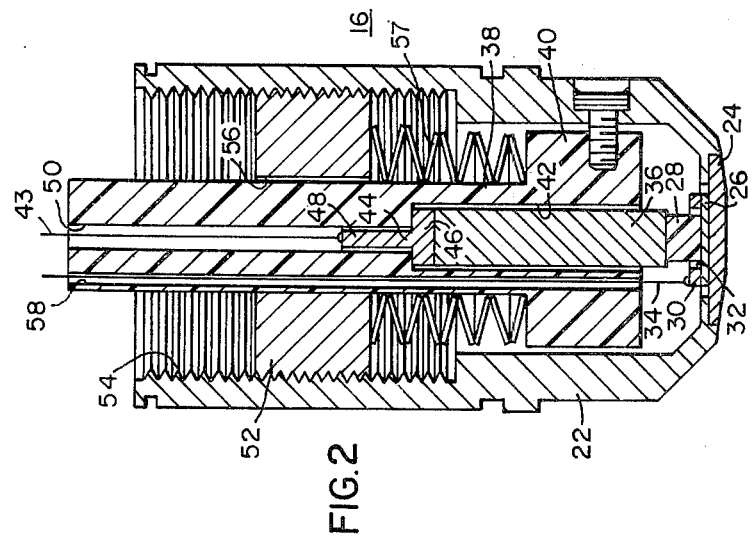

REPLACEABLE ACOUSTIC TRANSDUCER ASSEMBLY

BACKGROUND OF THE INVENTION

The use of electroacoustic sensor elements for use as flow meter detectors, and flaw detectors in metal vessels has been widespread. In its simplest form, a piezoelectric element is acoustically coupled to the medium which is to be sensed, and the electrical signal derived therefrom indicates the condition of the medium under study. Acoustic emission transducers have been proposed for use as passive listening devices to detect the noise being emitted by growing flaws, as for example in monitoring the metal wall for a nuclear reactor pressure vessel. Such electroacoustic transducers are affixed to the exterior pressure vessel wall and remain in place for monitoring of the vessel wall condition during operation. For such usage, the tranducer assembly must be able to withstand the high temperature and the high radiation flux level associated with the reactor vessel. The use of a metallic high temperature resistant protective enclosure member about the active electroacoustic transducer element for such applications is essential. A thin metallic acoustic window is provided at one end of the transducer assembly, and this window is mechanically and acoustically coupled to the vessel wall which is to be sensed or inspected. In order to insure high reliability and sensitivity it is essential that efficient acoustic coupling be achieved between the metallic window member and the electroacoustic transducer element supported within the enclosure. It has also been the practice to acoustically couple the interiorly disposed surface of the piezoelectric electroacoustic element to a damping block which minimizes the ringing of the signal produced. In copending application Ser. No. 264,663, filed June 20, 1972 a severe environment acoustic transducer is described in which a polyimide organic adhesive is used to adhere the active transducer elements together and to retain the transducer elements in place in a fixed relationship. Such a device required careful mechanical and chemical preparation of the mating surface of the various active transducer elements as well as the metallic acoustic windows.

SUMMARY OF THE INVENTION

An easily replaceable, severe environment electroacoustic transducer assembly comprising a generally tubular enclosure member, having a transducer window sealingly provided at one end of the enclosure member, which window is adaptable to the medium to be tested. A piezoelectric element is acoustically coupled to the transducer window, which is in turn acoustically coupled to an elongated electrically conductive mechanical energy damping element. An elongated insulating plug fits within the tubular enclosure member about the damping element, and compressive means are integrally disposed within the enclosure member for compressively holding the insulating plug against the damping element, to thereby compress the damping element against the piezoelectric element, this ensure that acoustic coupling is maintained and that the damping element is protected against damage due to impact induced mechanical shock. A pair of electrical conductors extend through the insulating plug, with one of the conductors electrically connected to one side of the piezoelectric element and the other conductor electrically connected to the conductive damping element.

BRIEF DESCRIPTION OF THE DRAWINGS

FIG. 1 is a side elevational view of the transducer assembly of the present invention in contact with a metal vessel.

FIG. 2 is a cross sectional view of the front end assembly of the transducer assembly of the present invention.

FIG. 3 is an electrical schematic showing the electrical characteristic of the elements that make up the transducer assembly.

DESCRIPTION OF THE PREFERRED EMBODIMENT

The present invention can be best understood by reference to the exemplary embodiments in the drawing.

In FIG. 1, the transducer assembly 10 is shown in position against a metallic vessel wall 12. The transducer assembly 10 is maintained in contact with the vessel wall 12 by means of spring loaded retaining means 14 which may be connected to the vessel wall 12 mechanically, or may be held in place by a magnetic coupling means, not shown. The retaining spring 15 extends between member 14 and flange 17 provided about front end assembly 16.

The transducer assembly 10 comprises a front end assembly 16, a flexible conduit portion with end fittings 18, and a transformer housing end portion 20.

The front end assembly 16 is seen in greater detail in FIG. 2. The front end assembly 16 comprises a generally tubular high temperature resistant metallic enclosure 22. The enclosure member 22, is typically formed of Kovar, which is a nickel-iron-cobalt alloy and is a trademarked material of the Westinghouse Electric Corporation, and is high temperature resistant and generally chemically resistant. Other nickle-iron alloys can be utilized. The conductive metal enclosure member 22 is also electrically grounded and serves as a shield to prevent generation of ground loops in the sensing circuitry. A high temperature resistant metallic transducer window 24, which is here a thin disc of metal, is brazed in place at one end of the enclosure member 22. The shield window 24 is also made of Kovar, which is readily brazed to ceramic and to other Kovar parts. A disc-like insulative ceramic window 26, which is metallized on both major surfaces is brazed to the interior surface of the end window 24. The insulative disc window 26 is formed of aluminum oxide, a ceramic material which has a high sound velocity and a good specific acoustic impedance match to the metal acoustic window 24. Aluminum oxide also exhibits a very low level value of ultrasonic attenuation and a relatively low dielectric constant. The metallic shield window 24 is a relatively thin member having a maximum thickness of about 0.03 inches and a structural contact diameter of about 0.13 inches. The structural surface contact area is the portion of the transducer's exterior surface that is in acoustic contact with the structure being tested, such as a pressure vessel wall. The structural surface contact diameter of the window is chosen to be about equal to ½ of the wavelength of a Rayleigh wave surface wave in steel at a frequency of about 500 kilohertz. A convenient operative frequency range for the transducer assembly in the present invention has been found to be from about 300 to 700 kilohertz. The window's structural surface contact diameter is not critical, but larger contact diameters could reduce sensitivity because of wave cancellation, while significantly smaller diameter would reduce sensitivity by restricting the size of the aperture through which acoustical energy is permitted to pass. The window's structural surface contact diameter is selected also to achieve a good acoustic coupling by pressing the face of the transducer against the vessel wall 12 with a compressive force, of for example about 30 pounds, provided by the spring loaded retaining means 14. With such a compressive force, no liquid couplant is required. The 0.03 inch window thickness provides sufficient strength yet achieves good acoustic transmission that is free of standing wave problems. It is preferred that the parallel surfaces of the metal window 24 be flat and have a surface finish of about 8 microinch to insure good acoustic coupling of the small diameter surface to the test structure, and good brazing of the large diameter surface to the alumina ceramic. The insulating alumina disc window 26 is typically about 0.2 inch in diameter with a thickness of about 0.025 inch. The diameter of window 26 is chosen to be compatible with the piezoelectric disc 28 to which it is brazed. The insulating disc window 26 thickness is selected to be much smaller than the wavelength of sound in alumina at a frequency of 500 kilohertz. The alumina disc 26 is metallized on both major surfaces by the well known molymanganese process, whereby refractory metals are chemically bonded to the normally inert alumina at a highly elevated temperature in a hydrogen atmosphere, and thereafter nickel plated. The nickel plating serves both to protect the refractory metal from oxidizing during high temperature transducer operation and to provide easy wetting during brazing of the insulating disc to the metal window 24.

A transducer negative electrical connection terminal 30, which is a ring-like member of approximately the same overall diameter as the insulating disc 26 is brazed to the insulating disc, and has an aperture 32 through the center thereof. Electrical lead-in 34 is connected to negative ring-like electrical connection terminal 30. The ring-like negative terminal 30 is also made of Kovar material and the inner diameter of the aperture 32 is such as to receive the piezoelectric disc 28 therein. One end of the piezoelectric disc 28 is thus in contact with the metallized surface of the insulating disc window 26. The piezoelectric or piezoceramic disc 28 has the typical dimension of about 0.1 inch diameter, and about 0.075 inch thickness, which values are selected to produce the best electroacoustic performance in the operative frequency band of 300 and 700 kilohertz. The pieozoelectric disc 28 is for example, made up of a lead-zirconate-titanate class of piezoceramic material which is commercially available as "G1500" from Gulton Industries, or as "PZT-5A" from the piezoelectric division of Vernitron Corporation. The piezoceramic discs are electrically poled along the axial direction. These materials have high sensitivity, resistivity, and stability over a wide temperature range. As will be explained later, with reference to the electrical schematic the transducer electroacoustic sensitivity is relatively insensitive to temperature.

A rod-like damping block 36 is disposed in line with the piezoelectric disc 28 and contacts it at one end surface. The damping block 36 is an electrically conductive material such as graphite or carbon-graphite composite materials which are selected for good ultrasonic mechanical damping properties, good electrical conductivity, moderate to high compressive strength, and good oxidation resistance at elevated temperatures. It is important to grind the end surface of the damping block which makes contact with the piezoelectric disc flat with an 8 microinch surface finish. This is to facilitate dry acoustic coupling of the damping block to the piezoelectric element. Graphite has been found to be a particularly good conductive damping material and improves the sensitivity of the device by minimizing ringing.

An elongated insulating plug 38 is fitted within the enclosure member 22 about the damping block 36. The insulating plug 38 has a large diameter end portion 40 at the forward end near to the piezoelectric element. A damping block receiving chamber 42 is provided centrally through the large diameter end portion 40 of the insulating plug 38. This chamber 42 is continued through a small diameter centrally extending chamber 50 which serves to permit passage of an electrical lead-in through the insulating plug 38. A positive electrical lead-in 43 is directed thereto and connected to positive electrical terminal 44, which is a conductive metal member having a flattened end surface with a diameter approximately equal to that of the damping block 36 and in abutting relationship therewith. The positive metal electrode terminal 44 is a piston like member having a head portion 46 and a rod-like portion 48. The head portion 46 and the damping block member 36 fit within the elongated damping block receiving chamber 42 provided within the insulating plug 38.

An externally threaded forcing plug 52 is threadedly engaged with the interior threaded surface 54 of the enclosure member 22 at the end removed from the window portion. A central aperture 56 is provided through the forcing plug, with the aperture diameter being sufficient to permit passage of the insulating plug therethrough. A high temperature disc spring means 57 is provided about the insulating plug 38, extending between the forcing plug 52 and the enlarged diameter end portion 40 of the insulating plug 38. As the forcing plug 52 is tightened into place by engagement with the threaded surface 54 of the enclosure member 22, the disc spring is compressed and acts to hold the transducer assembly portions within the enclosure member together under compressive force. A disc spring provided a relatively high compressive force in a short range of motion while occupying a small space. A number of disc springs may be mechanically joined in series to provide the desired compressive force, which is for example about 17 pounds which provides a corresponding total compressive stress acting over the 0.1 inch diameter piezoelectric disc of about 2160 psi. A lead-in aperture 58 is provided along the length of the insulating plug 38 to permit passage of the negative electrical lead-in 34 which is connected to the negative electrical terminal 30.

The brazing alloy utilized between the metal window 24, the insulating disc window 26, and provided upon the surface of the insulating disc to which the piezoelectric disc is compressively joined contains a percentage of a relatively malleable metallic constituent, such as palladium which provides sufficient mechanical compliance to insure that a void free acoustically transparent butt joint is formed. The brazing alloy which has been found acceptable is available under the trademark "PALCUSIL-10" available from Western Gold and Platinum Company. The nominal composition of Palcusil-10 is 58% silver, 32% copper, and 10% palladium. Its liquidus is 852°C (1566°F) and its solidus is 824°C (1515°F). The brazing alloy is used in a preform disc of about 0.2 inch diameter and about 0.001 inch thickness. Upon heating the brazing alloy mechanically bonds the insulating disc window 26 to both the metal window 24 and ring-like negative terminal 30. In addition, the brazing alloy coats the exposed surface of the insulating disc window 26, thereby facilitating effective subsequent dry acoustic coupling of the piezoelectric disc 28 to the insulating disc window 26, particularly due to the compressive stress exerted thereon by the disc spring means 57.

An elongated flexible metal conduit member 18 is sealed to the open end of the generally tubular enclosure member 22, and the positive and negative electrical lead-ins are carried through this flexible conduit 18. The flexible conduit comprises a 0.25 inch inner diameter stainless steel airtight bellows overlaid with a double braided stainless stainless steel jacket and is provided with solid tubular end fittings. The conduit is hermetically sealed to the enclosure member 22. A transformer housing end portion 20 is hermetically sealed at the other end of the flexible conduit 18, and comprises a generally tubular body within which is disposed a pot core transformer. The transformer is chosen to match the electrical output impedance of the piezoelectric element to the impedance of the transmission line which carries the signal to the electronic sensing system. A hermetically sealed enclosure member 60 is provided at the end of the transformer housing end portion 20 and electrical outputs are insulatingly brought through this end member 60 to permit connection of the transducer assembly to the transmission line.

An electrical schematic of the transducer assembly 10 is seen in FIG. 3, wherein the composite structure comprising the enclosure member 22, the metallic window 24, the conduit 18, the transformer housing end portion 20, and enclosure member 60 is represented as the electrically grounded enclosure wall. Which are in serial electrical connection with the metallized alumina acoustic window, the electrical capacitance of which is represented as $C_W$ in this Figure. The electrical output impedance of the piezoelectric crystal is complex due to the many mechanical resonances occupying the frequency band of interest, for this reason, it is represented by the blocked function $Z_C$. The electrical signal generated in the crystal is shown as $E_C$, the electrical capacitance between the positive and negative electrical leads is equal to $C_{PN}$. The capacitance between the positive lead and shield, and between the negative lead and shield are shown as $C_{PS}$ and $C_{NS}$ respectively. The inductance $L_p$ represents the primary winding open circuit inductance of the transformer, and C is the total winding capacitance of the transformer referred to the primary side, and $N_P$ is the number of turns in the primary winding, and $N_S$ is the number of turns in the secondary winding. The center point of the secondary winding is shown as being grounded so that the transformer output is balanced electrically with respect to ground. The conductive enclosure member 22, the conductive flexible conduit 18, and the conductive transformer comprises the electrically grounded shield assembly outlined in FIG. 3 about the active components.

The termination resistor $R_O$ is selected to match the impedance of the transducer assembly. It has been the normal practice to connect the transducer output directly to a high input impedance amplifier, rather than to terminate the line as seen in FIG. 3 and take the output across the resistor $R_O$. It has been discovered that such a termination eliminates the large variation of sensitivity with temperature which had heretofore been observed. With this loading arrangement, the transducer's electroacoustic sensitivity is relatively insensitive to temperature. The sensitivity of the device decreases by only about 1.5dB when the operating temperature is raised from room ambient to 550°F.

What we claim is:
1. An acoustic transducer assembly comprising:
   a generally tubular metal enclosure member,
   a transducer window and piezoelectric element assembly sealingly disposed at one end of the tubular enclosure, wherein the transducer window is a high temperature resistant metal disk sealed to the tubular enclosure member with a high acoustic energy transmissive thin insulating disk acoustically coupled to the interior surface of the metal disk, and the piezoelectric element is a thin disk acoustically coupled to the other side of the insulating disk,
   an elongated conductive acoustic energy damping element in contact with the side of the piezoelectric element facing inwardly within the tubular enclosure member,
   an elongated insulating plug fitting within the tubular enclosure member about the damping element,
   compressive spring means within the enclosure member for compressively holding the insulating plug against the damping element and thereby compressing the damping element against the piezoelectric element,
   a pair of electrical conductors extending through the insulating plug, one conductor electrically connected to one side of the piezoelectric element, the other conductor electrically connected to the conductive damping element,
   a closure plug movably fitted in the other end of the tubular metal enclosure member, which plug is movable along the axis of the tubular metal enclosure member to engage one end of the compressive spring means, which thereby compresses the damping element against the piezoelectric element which is in turn compressed against the transducer window, which compression means thereby electrically and acoustically couples the damping element, the piezoelectric element and the transducer window.

2. The transducer assembly specified in claim 1, wherein the elongated insulating plug comprises a generally cylindrical body with a damping element receiving chamber at one end, and an enlarged diameter portion at the end proximate the damping means with the spring means bearing against this enlarged diameter portion.

3. The transducer assembly specified in claim 2, wherein a positive electrode is fitted within the damping element receiving chamber of the insulating plug, which positive electrode has a flat surface which is compressively butted against the damping element.

4. The transducer assembly specified in claim 1, wherein both sides of the insulating disk are metallized with a refractory metal layer and a nickel plating layer atop the refractory metal layer.

5. The transducer assembly specified in claim 1, wherein the transducer negative terminal electrode comprising an annular metal member is disposed on the metallized surface of the insulating disk facing the piezoelectric element, with the piezoelectric disk disposed within the annular area defined by the electrode.

6. The transducer assembly specified in claim 5, wherein the transducer shield window, the metallized insulating disk, and the negative electrode are acoustically coupled together by butt braze joint, which braze material is high temperature resistant and mechanically complaint to ensure formation of a void free, acoustically transparent butt joint.

7. The transducer assembly specified in claim 6, wherein the braze material covers the metallized surface of the insulating disk compressed against the piezoelectric disk to effectively acoustically couple these elements together.

8. The transducer assembly specified in claim 7, wherein the braze material comprises a silver-copper mixture which is alloyed with a small amount of palladium.

9. The transducer assembly specified in claim 1, wherein the end of the damping element in compressive contact with the piezoelectric element is ground flat to permit effective dry acoustical coupling therebetween.

10. The transducer assembly specified in claim 1, wherein the damping element comprises a cylindrical body of graphite.

11. The transducer assembly specified in claim 1, wherein the tubular metal enclosure member serves as a grounded shield which is sealingly connected to a flexible hermetically sealed ground conduit within which the pair of electrical conductors are continued as a transmission cable which extends into a sealed generally tubular transformer housing, with a transformer having an impedance which matches the impedance of the piezoelectric element disposed within the generally tubular transformer housing, with the primary windings of the transformer electrically connected to the conductors of the transmission cable, and the secondary windings connected to output conductors which are sealingly brought through the closed end of the transformer housing.

12. The transducer assembly specified in claim 11, wherein the output conductors are terminated with a resistor which matches the impedance of the transducer assembly.

13. An acoustic transducer assembly comprising:
a generally tubular metal enclosure member,
a transducer window and piezoelectric element assembly sealingly disposed at one end of the tubular enclosure,
an elongated conductive acoustic energy damping element in contact with the side of the piezoelectric element facing inwardly within the tubular enclosure member,
an elongated insulating plug fitting within the tubular enclosure member about the damping element, which elongated insulating plug comprises a generally cylindrical body with a damping element receiving chamber at one end, and an enlarged diameter outer shoulder portion at the end proximate the damping means,
a compressive spring means disposed about the elongated insulating plug, with one end of the spring bearing against the outer shoulder portion of the plug, and the other end of the spring means being compressed by a closure plug movably mounted within the tubular metal enclosure member, and movable along the axis of the tubular member to apply a predetermined compressive force on the insulating plug, which in turn engages the damping element to compress the damping element against the piezoelectric element,
a pair of electrical conductors extending through apertures provided in the insulating plug, one conductor electrically connected to the outwardly disposed side of the piezoelectric element, the other conductor electrically connected to the conductive damping element which compressively electrically contacts the inwardly disposed side of the piezoelectric element.

14. The transducer assembly specified in claim 13, wherein a positive electrode is fitted within the damping element receiving chamber of the insulating plug, with the one electrical conductor connected to the positive electrode which has a flat surface which is compressively butted against the damping element.

* * * * *